United States Patent [19]
Doherty et al.

[11] Patent Number: 5,441,071
[45] Date of Patent: Aug. 15, 1995

[54] AUTOMATED WATER SAMPLE COLLECTING SYSTEM

[75] Inventors: Kenneth W. Doherty, West Falmouth; Susumu Honjo, Falmouth; John D. Billings, North Falmouth, all of Mass.

[73] Assignee: McLane Research Laboratories, Inc., Monument Beach, Mass.

[21] Appl. No.: 238,150

[22] Filed: May 4, 1994

[51] Int. Cl.$^6$ .................. G01N 1/14; F16K 11/074
[52] U.S. Cl. ..................... 137/15; 137/240; 137/625.11; 73/864.35
[58] Field of Search ............ 137/15, 240, 625.11; 73/864.34, 864.35

[56] References Cited

U.S. PATENT DOCUMENTS

| | | | |
|---|---|---|---|
| 3,380,591 | 4/1968 | Muller | 210/143 |
| 3,703,465 | 11/1972 | Reece | 210/333.1 |
| 3,896,637 | 7/1975 | Audouze et al. | 73/864.34 X |
| 3,924,471 | 12/1975 | Singer | 73/864.35 |
| 3,995,494 | 12/1976 | Muller et al. | 137/625.11 X |
| 4,037,472 | 7/1977 | Gates | 73/864.35 |
| 4,163,392 | 8/1979 | Fleenor et al. | 73/864.35 |
| 4,350,429 | 9/1982 | Slavin | 137/625.11 X |
| 4,430,220 | 2/1984 | Litzenburger | 210/333.1 |
| 4,540,015 | 9/1985 | Henriksen et al. | 137/625.11 X |
| 4,702,889 | 10/1987 | Cabrera et al. | 137/240 X |
| 5,167,802 | 12/1992 | Sandstrom | 137/625.11 X |
| 5,197,340 | 3/1993 | Jones | 73/864.35 |
| 5,296,197 | 3/1994 | Newberg et al. | 137/240 X |

FOREIGN PATENT DOCUMENTS 3134722  3/1983  Germany ................. 73/864.35

Primary Examiner—John Rivell
Attorney, Agent, or Firm—Daniel H. Kane

[57] ABSTRACT

An automated water sampling system collects multiple samples of sample water at a remote site. A multiport valve provides a plurality of ports and respective port inlets. A sample water intake line is coupled to the respective port inlets. A plurality of sample receivers or sample containers are coupled to respective ports of the multiport valve. At least one container of cleaning liquid is also coupled to a port of the multiport valve. An output manifold provides a plurality of manifold outlets coupled to the respective sampler receivers and to at least one container of cleaning liquid. A pumping water output line is coupled to the plurality of manifold outlets. A reversible pump is coupled in the water output line for pumping and drawing sample water through the intake line into selected sample receivers and for pumping and pushing cleaning liquid from said at least one cleaning liquid container out the sample water intake line. The multiport valve opens and closes the ports one at a time. The water sample receivers are each constructed as an elongate container having a sample water opening at one end, a pumping water opening at the other end, and a slidable sealing piston container within and slidable between the ends of the elongate container in response to differential pressure across the piston. The cleaning liquid container is similarly constructed and a flushing liquid container may also be coupled to a port of the multiport valve for flushing away the cleaning liquid.

21 Claims, 6 Drawing Sheets

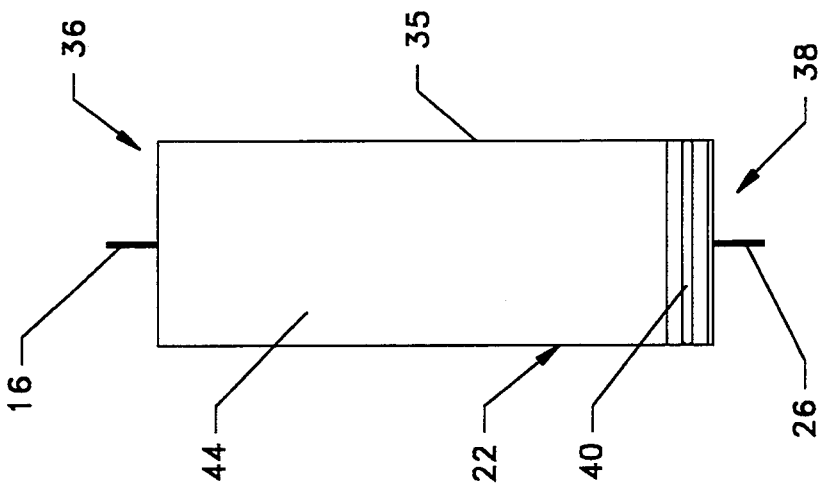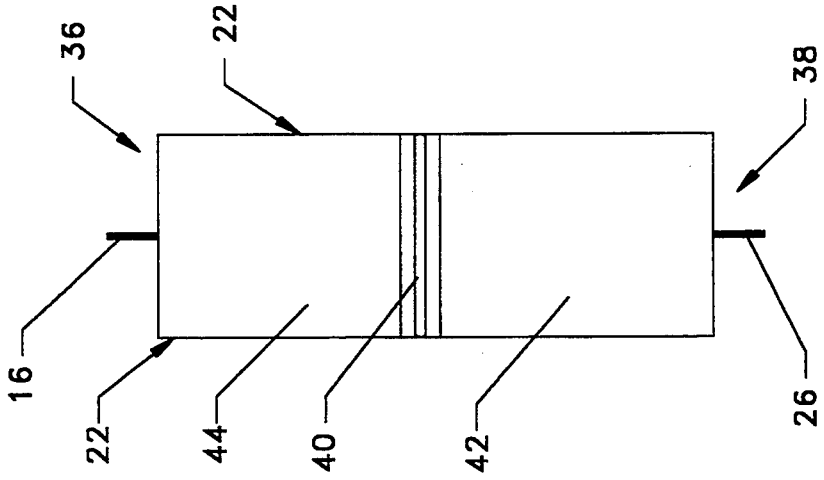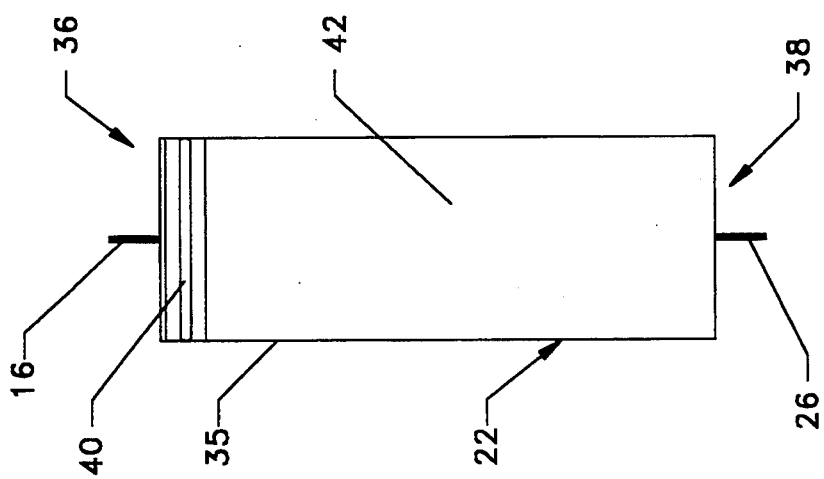

AUTOMATED WATER SAMPLE COLLECTING SYSTEM

CROSS REFERENCE TO RELATED PATENT APPLICATION

This invention is related to U.S. patent application Ser. No. 08/122,384 filed Sep. 16, 1993 for "MULTIPORT VALVE FOR FLUID TRANSFER SYSTEMS". The coinventors and assignee of the related patent applications are the same.

TECHNICAL FIELD

This invention relates to a new time series water sample collecting system for collecting water samples of specified volume at programmed intervals in a submarine or subaqueous environment. The invention is particularly applicable for use at remote locations. The water sample collecting instrument is operated by a programmable controller for fully automated operation. Between the water sample collecting events, a reversible pump and multiport valve are controlled to dispense cleaning liquid such as an acid through the water sample intake line to wash away biofouling material and minimize contamination of samples. The acid wash is then flushed away by distilled water. The system is applicable for collecting water samples in oceans, lakes, or rivers for a wide variety of analyses and studies, e.g. nutrient levels, $CO_2$ concentration, dissolved organic matter, trace elements, pollutants, etc.

BACKGROUND ART

A variety of multiport valve mechanisms have been developed for backwashing filters. For example, the Reece et al. U.S. Pat. No. 3,703,465 issued in 1972 for a "Filter With Rotating Backwash Selector" describes a filter assembly with multiple filter elements arranged in a circular ring configuration. All of the filter elements of the Reece et al. device are used at once for simultaneously filtering a liquid flow.

According to Reece et al. the backwash mechanism incorporates a rotatable inlet channel and a rotatable outlet channel which can be stepped in synchronism from filter element to filter element and coupled respectively to the ends of each elongate filter holder. A separate backwash fluid can then be flushed through the selected filter element in a backward direction while the other filter units continue to be used for regular filtration in a forward direction. The backwash valve of Reece et al. is then stepped by a motor and drive from filter unit to filter unit for sequentially cleaning the filter assembly.

A disadvantage of the Reece et al. backwash selector is that it is not applicable for use with sample collecting systems using sample collecting tubes, bottles, syringes or bags intended for one way receipt of liquid. Nor is the Reece et al. device designed for submerged, subaqueous, or submarine use.

The Litzenburger U.S. Pat. No. 4,430,220 describes a similar device for selective channeling of backwash fluid for flushing out filter elements. In the Litzenburger apparatus the filter elements are also arranged in a radial sequence. A hollow rotary valve is connected to the respective ends of the filter elements in rotary sequence for backflushing. The Muller U.S. Pat. No. 3,380,591 describes another fluid filter assembly with an automatic cleaning device for backflushing and cleaning filter elements. Again neither of these devices is designed for filling sample collecting devices which ordinarily accept only a one way flow, nor are they designed for use in submarine or subaqueous environments.

The Sandstrom U.S. Pat. No. 5,167,802 describes a distributor valve which provides selective connection from a sample pump to a plurality of different collection units. The collection units include filters for removing particulate matter from water, for example collected from a river, and sample water collecting bottles. Water samples are collected automatically in response to a given condition or a passage of a preselected time period. The Sandstrom system provides both a sample operating mode for collecting samples, and a purge operating mode using a cleaning liquid. Alternation between the sampling mode and purging mode is accomplished by a four way valve.

The sample pump is connected between the water source and a distributor valve with one inlet port and forty-eight outlet ports of alternating sample outlet ports and purge outlet ports. Each sample outlet port leads to a collection unit and each purge port is for waste disposal. The distributor valve with forty-eight outlet ports is driven by a valve motor with a pawl and notch assembly which rotates an inlet disk to align the inlet port with one of the plurality of peripheral outlet ports. A timer computer controls the intermittent rotation of the disk.

The entire Sandstrom system however is arranged in the air and is not submerged. The Sandstrom system does not address the problems of submerged marine operation and cannot operate in the subaqueous or submarine environment. Furthermore it appears that a primary purpose of the purge operating mode is to clean the pump with methanol because the sample pump is interposed between the sampled source of water such as a river, and multiple sample receivers or collectors.

Another disadvantage of such multiport valve purging systems is that no provision is made for removing and diluting the cleaning liquid. Thus, the cleaning liquid itself may become a source of contamination in the case of a timed sequence of repeated sample collecting events using the same equipment.

OBJECTS OF THE INVENTION

It is therefore an object of the present invention to provide a time series water sample collecting system for automatically collecting water samples at programmed intervals and at remote locations in submarine or submerged environments. The invention is intended for collecting samples in one way receivers such as sample collecting tubes, bottles, syringes or bags.

Another object of the invention is to provide a water sample collecting system without interposing a pump or other similar source of contamination between the sample water intake line and sample collectors. A downstream pump is instead used to draw sample water into sample collectors.

A further object of the invention is to provide a sample water collecting system with provision for washing away biofouling material in the sample water inlet line between sample collecting events. To this end, a cleaning liquid is flushed out the sample water intake line prior to collecting a sample. A related object of the invention is to provide active flushing away of the cleaning liquid in preparation for the next sample collecting event to avoid contamination by the cleaning liquid.

DISCLOSURE OF THE INVENTION

In order to accomplish these results the invention provides an automated water sampling system for collecting multiple samples of sample water at a remote site. A multiport valve provides a plurality of ports and respective port inlets. A sample water intake line is coupled to the respective port inlets. The multiport valve is constructed for individually opening and closing the port inlets. A plurality of sample receivers or sample containers are coupled to respective ports of the multiport valve. At least one container of cleaning liquid is also coupled to a port of the multiport valve.

According to the invention an output manifold provides a plurality of manifold outlets coupled to the respective sample receivers and to said at least one container of cleaning liquid. A pumping water output line is coupled to the plurality of manifold outlets. A reversible pump is coupled in the water output line for pumping and drawing sample water through the intake line into selected sample receivers and for pumping and pushing cleaning liquid from said at least one cleaning liquid container out the sample water intake line.

A programmable controller is coupled to the multiport valve and pump for fully automated operation. The controller is programmable to cause pumping and drawing of sample water into the intake line and into respective sample receivers in series in a timed sequence of sample collecting events. The controller is also programmable for reversing the pump and pumping and pushing cleaning liquid from at least one cleaning liquid container out the intake line to wash away biofouling material between the sample collecting events.

In the preferred example embodiments the water sample receivers are each constructed as an elongate container having a sample water opening at one end, a pumping water opening at the other end, and a slidable sealing piston contained within and slidable between the ends of the elongate container in response to differential pressure across the piston. Each elongate container is coupled to a respective port of the multiport valve at the sample water opening end and to a respective manifold outlet of the output manifold at the pumping water opening end.

At least one cleaning liquid container is also constructed as an elongate container having a cleaning liquid opening at one end and a pumping water opening at the other end. A slidable sealing piston is contained within and is slidable between the ends of the elongate container in response to differential pressure across the piston. The elongate container of cleaning liquid is coupled to a respective port of the multiport valve at the cleaning liquid opening end and to a respective manifold outlet of the output manifold at the pumping water opening end.

The initial position of the piston in respective sample receivers before a respective sample collecting event is adjacent to the sample water opening end of the elongate container. The elongate container is back filled with pumping water from the pumping water opening end. The starting position of the piston in the cleaning fluid container is adjacent to the pumping water opening end with the elongate container filled with cleaning liquid.

The invention contemplates a variety of embodiments in which the sample receivers can be syringes, elongate cylindrical sample collecting tubes, and flexible bags. In the flexible bag embodiment, each flexible bag is enclosed within the elongate container with an opening coupled to the respective port through the sample water opening end of the elongate container.

The multiport valve is generally constructed with a valve head having multiple ports and port inlets arranged in substantially circular configuration. A distributor rotor bears against the valve head for rotation to different rotational positions. The rotor forms a seal between the rotor and valve head. The distributor rotor is formed with a coupling channel for coupling the sample water intake line to different port inlets and respective ports according to the rotational position of the rotor.

In the preferred example the valve head and distributor rotor are formed with flat bearing faces for sealing and closing all port inlets and ports when the rotor is in rotational positions with the coupling channel between ports. The bearing face of the valve head is formed with a circular channel having a first diameter coupled to the water sample intake line. The bearing face of the valve head is also formed with a circle of holes providing the port inlets. The port inlet holes are arranged in a circular ring having a second diameter different from the first diameter of the circular channel but concentric with the circular channel. The circular ring of port inlet holes may actually be arranged in a double ring to accommodate larger numbers of port inlet holes for multiport valves with many ports. The bearing face of the rotor is formed with a radial coupling channel extending in a radial direction between the circular channel and circular ring of port inlet holes of the valve head.

A cleaning liquid container of cleaning liquid is also coupled to a cleaning port of the multiport valve for washing away biofouling material from the sample water intake line. Another elongate container of flushing liquid is coupled to a flushing port of the multiport valve for flushing away cleaning liquid. The controller is programmable for operating the pump in reverse for first pumping and pushing cleaning liquid out the sample water intake line and then pumping and pushing flushing liquid out the sample intake line for flushing away the cleaning liquid.

The invention also provides a new method for automatically sampling water at a remote site using a multiport valve having a plurality of ports and respective port inlets. The method is composed of steps for alternately collecting water samples and cleaning and flushing the sample water intake line between the sampling events. Other objects, features and advantages of the invention are apparent in the following specification and accompanying drawings.

BRIEF DESCRIPTION OF THE DRAWINGS

FIGS. 2, 3, & 4 are detailed side diagrammatic views of a water sample collecting tube with sliding piston according to the invention showing in sequence three stages namely before, during and after a water sample collecting event. In opposite sequence, FIGS. 4, 3, & 2 show operation of the cleaning liquid container and flushing liquid container during an entire cycle of a plurality of water sampling events.

DESCRIPTION OF PREFERRED EXAMPLE EMBODIMENTS AND BEST MODE OF THE INVENTION

Figure 1:
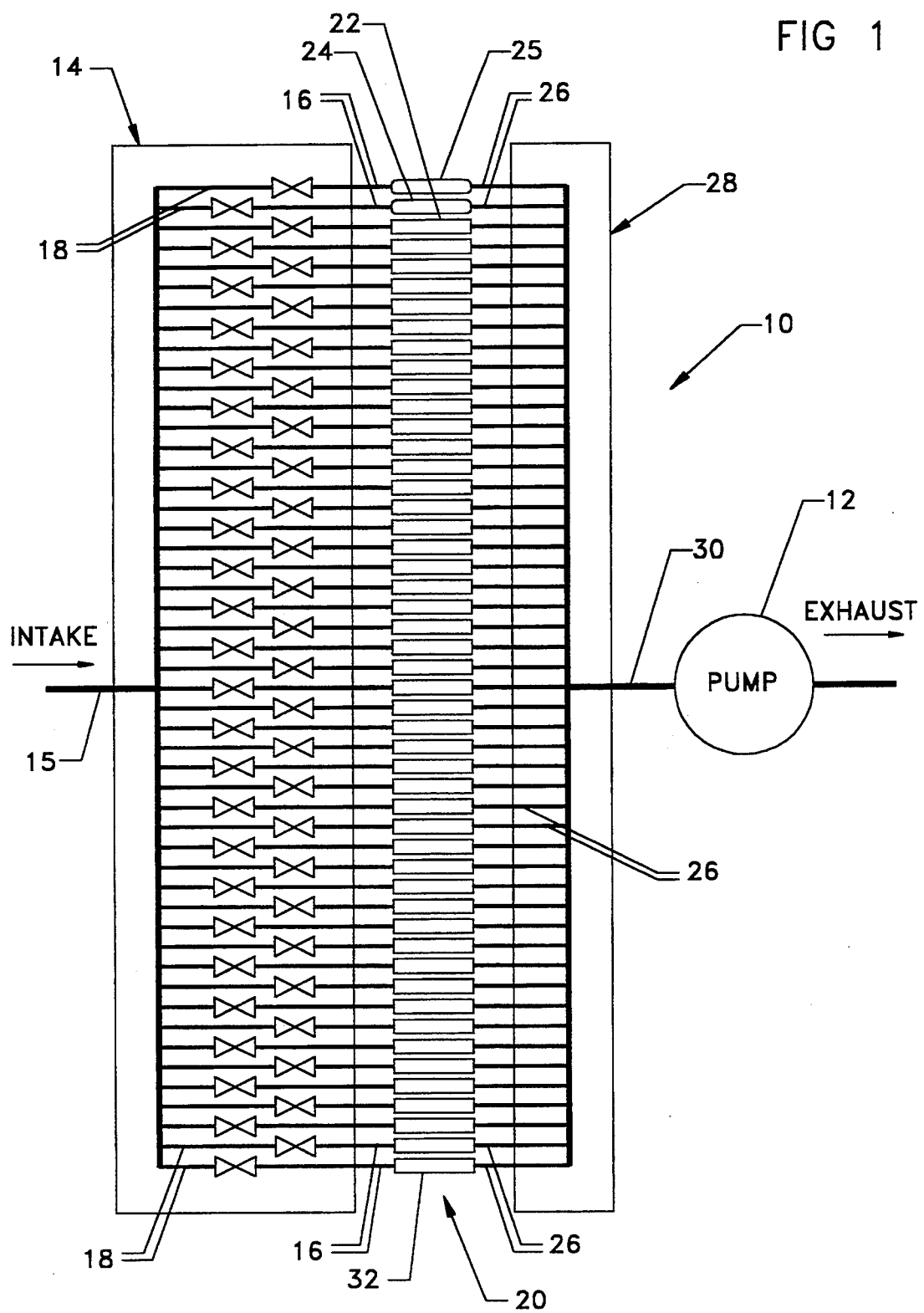
FIG. 1 is a Simplified diagrammatic view of the water sample collecting system according to the invention.

A simplified schematic diagram of the elements of the automated water sampling system (WSS) 10 according to the invention is illustrated in FIG. 1. The pump 12 such as a precision graphite gear pump is positioned on the down stream side of the WSS 10 for drawing water samples through the WSS to avoid contamination of the water samples. The pump 12 is driven, for example, by a three phase DC motor. Because the water sample containers are of relatively small fixed volume, the flow rate can be set at a relatively low value for example, 30 ml/min.

On the upstream side of the automated water sampling system 10 is a single head multiport valve assembly shown diagrammatically in block 14. The multiport valve 14 has a single valve head with an intake port 15 through which the sample water or other fluid to be sampled is drawn by pump 12. The multiport valve 14 is constructed with a plurality of ports 16 and corresponding port inlets 18. The sample water intake line 15 is coupled to the respective port inlets 18. As hereafter described the single head multiport valve 14 is constructed for individually controlling, opening and closing the port inlets 18 to respective ports 16. According to the operation of the single head multiport valve 14, only one of the port inlets 18 and respective port 16 is opened at a time by the multiport valve assembly. In the example of FIG. 1 the multiport valve assembly 14 is shown with fifty ports 16 and corresponding respective port inlets 18.

The multiport valve assembly 14 is coupled to a bank 20 of water sample receivers, collectors or containers 22. In the example of FIG. 1 forty-eight water receivers 22 are shown coupled respectively to 48 of the ports 16 of the multiport valve 14. The water sample containers 22 are coupled to the respective ports 16 at the water sample inlet ends of the respective water sample containers 22. The remaining two ports on the fifty ports of multiport valve 14 are coupled respectively to a cleaning liquid container 24 and a flushing liquid container 25 all as hereafter described in further detail.

On the downstream side of the water sample receivers or containers 22, the pumping water ends of the water sample containers 22 are coupled to the respective manifold outlets 26 of an output manifold 28 indicated by block 28. The outlet manifold 28 is also formed with fifty manifold outlets 26. The pumping water end of the forty-eight water sample containers 22 are coupled to forty-eight of the respective manifold outlets 26 while the other two are coupled respectively to the pumping water ends of the cleaning liquid container 24 and flushing liquid container 25. A single pumping water outlet line 30 is coupled to the respective plurality of manifold outlets 26.

Gear pump 12 is a reversible pump coupled in the water outlet line 30 for pumping and drawing sample water through the intake line 15 into a selected sample receiver or container 22. The pump is reversible for pumping and pushing cleaning liquid from the cleaning liquid container 24 out the sample water intake line 15. The cleaning liquid is used to wash away biofouling material from the intake line 15. Similarly, the pump 12 operates in reverse to pump flushing liquid from the flushing container 25 out through the water sample intake port 15. The flushing liquid, typically distilled water, flushes cleaning liquid such as an acid cleaner from the intake line 15.

The water sample receivers or containers 22 may take the form of, for example, syringes, elongate cylindrical sample collecting tubes, flexible bags, etc. Syringes are typically used for low volume samples with the syringe body holding a water sample of e.g. 30 ml. For larger volume samples, tube containers are used in the configuration of long cylindrical tubes which can hold larger volume water samples of for example five liters. A third type of water sample container is a plastic bag such as a space shuttle bag which may hold a water sample of intermediate volume such as, e.g. 1 liter.

A preferred example of the invention using cylindrical collector tubes is illustrated in FIGS. 2, 3, and 4. In the example of FIG. 2 the sample water receiver 22 is formed with an elongate cylindrical container 35 closed at both ends but with an inlet/outlet passageway or opening at each end. At the water sample inlet end 36 of sample water receiver 22 the inlet/outlet passageway or opening is coupled to one of the ports 16 of multiport valve 14. At the pumping water outlet end 38 of sample water receiver 22 the inlet/outlet passageway or opening is coupled to one of the manifold outlets 26 of manifold 28.

The sample water container 22 is also fitted on the inside with a slidable sealing piston 40 contained within the cylindrical container 35 and slidable between the ends 36,38. The piston 40 slides between the ends of the elongate sample water container 22 in response to differential pressure across the piston 40.

The initial position of the piston 40 in respective sample receivers 22 before a sample collecting event is adjacent to the sample water opening end 36 of the elongate sample water container 22 as shown in FIG. 2. The sample water container is back filled with pumping water 42 from the pumping water opening end 38 which pushes the piston 40 against the sample water opening end 36.

As shown in FIG. 3 when sample water is to be collected in a particular water receiver 22, the multiport valve 14 under control of the programmable controller opens the respective port inlet 18 and port 16. The pump 12 operating in the normal forward mode draws pumping water 42 from the backfilled side of water sample receiver 22 through the pumping water opening end 38 and respective manifold outlet 26. The differential pressure across piston 40 causes the piston to slide from the sample water opening end 36 to the pumping water opening end 38 drawing sample water 44 into the sample water receiver 22 until it is filled with sample water 44 as shown in FIG. 4. In the filled or spent condition, the piston 40 rests against the pumping water opening end 38 of the water sample container 22 and all pumping water has been exhausted.

To understand the operation of the cleaning liquid container 24 and flushing liquid container 25, reference is made to the sequence of FIGS. 2–4 in reverse. Starting with FIG. 4, the cleaning liquid container 24 is initially filled with a cleaning liquid such as an acid cleaner. The piston 40 rests against the pumping water opening end 38 of the cleaning liquid container. The cleaning liquid container 24 may contain, for example, a 5 liter volume of acid cleaning liquid. Prior to each water sample collecting cycle, the pump 12 is reversed for an increment of time pushing the piston 40 an increment of distance along the length of the cylindrical cleaning liquid container 35. The piston 40 gradually makes its way toward the cleaning liquid opening end 36 of the cleaning liquid container 24 as shown in FIG. 3. The piston 40 finally reaches the cleaning liquid opening end at the end of all the water sampling events and at the end of the current life cycle of the WSS. Thus the cleaning liquid container 24 contains sufficient cleaning liquid for flushing biofouling material from the intake line 15 prior to each water sampling event for the entire forty-eight water sampling events of the multiport valve 14 and WSS 10 of FIG. 1.

Similarly the flushing liquid container 25 is filled with distilled water so that the piston 40 rests against the pumping water opening end 38 of the flushing liquid container 25 as shown in FIG. 4. After cleaning away any biofouling material from the intake line 15 using the acid cleaning liquid from cleaning liquid container 24, the multiport valve 14 under control of the programmable controller closes the cleaning liquid container 24 by closing the respective port 16 and port inlet 18 while opening the respective port 16 and port opening 18 for the flushing liquid container 25. The pump 12 operating in reverse pumps and pushes the piston 40 an increment of distance along the cylindrical container 35 of the flushing liquid container 25 for flushing away acid cleaning liquid from the intake line 15. Over the forty-eight water sampling events and the life cycle of the particular WSS the piston 40 within the flushing liquid container 25 gradually works its way toward the flushing liquid opening end 36 as shown in FIG. 3 and FIG. 2, viewing the sequence in reverse from FIG. 4, to FIG. 3, to FIG. 2.

Figure 5:
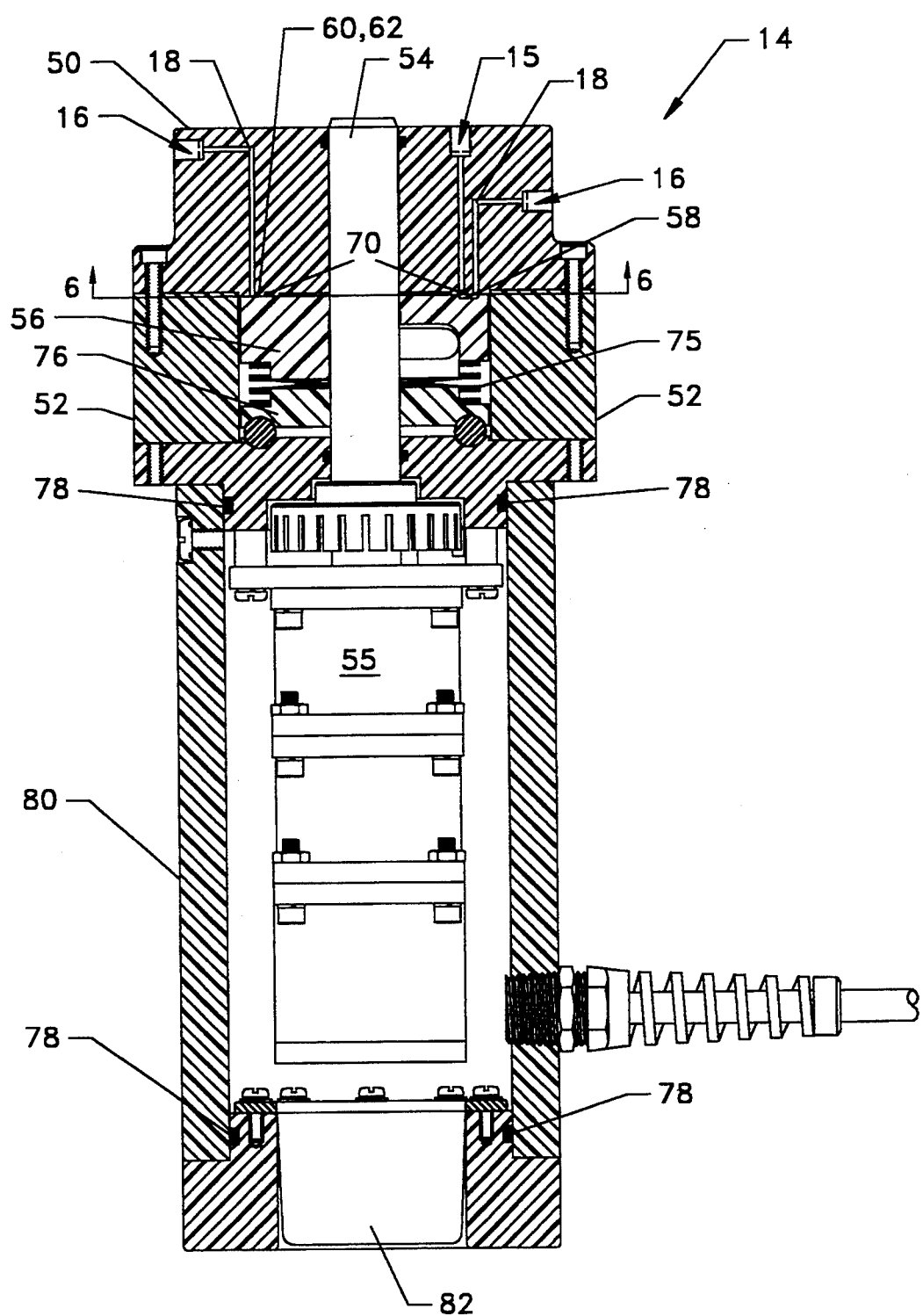
FIG. 5 is a detailed side cross section view of a single head multiport valve for controlling flow of sample water from the intake line to respective intake ports and sample collectors.

A preferred example implementation of the multiport valve assembly 14 is illustrated in FIG. 5. The multiport valve 14 is formed with a single valve head 50 and multiport valve body 52 which remain in stationary position relative to the water sampling system 10. A central coaxial rotating drive shaft 54 rotates within the valve head 50 and valve body 52 and is driven by stepper motor 55. The rotating drive shaft 54 turns a distributor rotor 56 formed with a radial coupling channel 58 to provide valve couplings in the valve head 50 between the single intake line 15 and multiple port inlets 18 and ports 16.

As shown in FIG. 5 the valve head 50 is formed with a single intake line 15 which may be coupled to any of the fifty port inlets 18 and respective ports 16 for coupling to the respective forty-eight water sample receivers 22, single cleaning liquid container 24 and single flushing liquid container 25.

The single intake line 15 is coupled to any one selected port 16 by the selected rotational position of the fluid distributor rotor 56 which is tied to the rotating shaft 54. The rotor 56 is formed with a bearing face 60 which bears against a complementary bearing face 62 of the valve head 50. The rotor 56 is formed with a radial coupling channel 58 which makes the fluid connection or coupling between the intake line 15 and a selected port inlet 18 and port 16.

Figure 6:
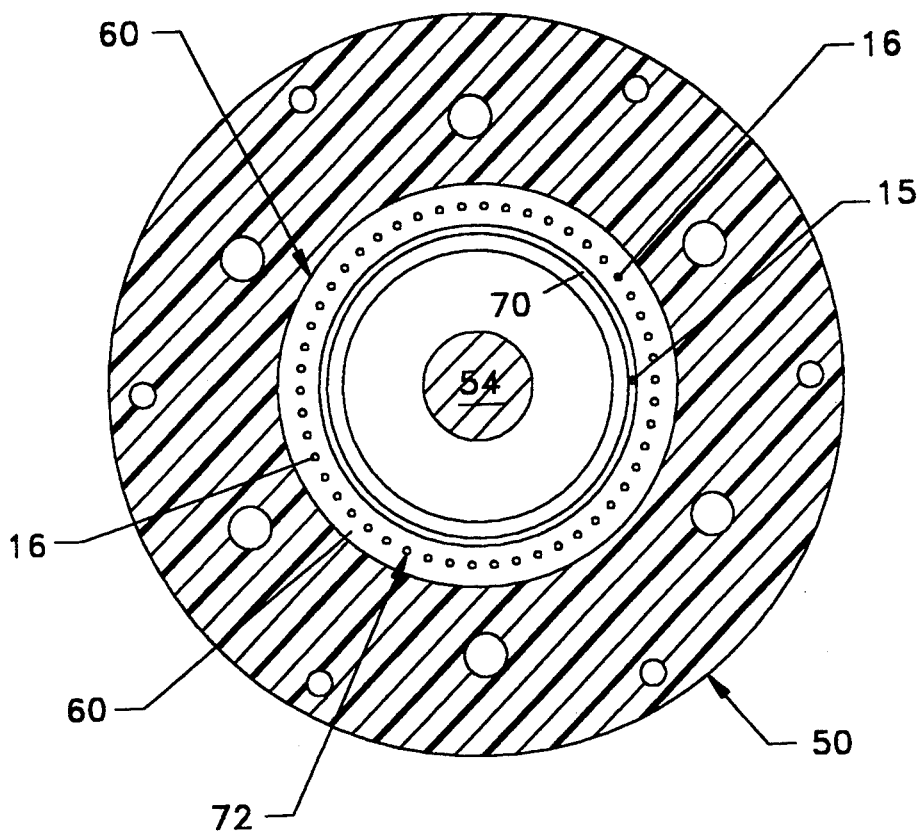
FIG. 6 is a detailed side cross section view of the multiport valve head showing the face of the valve head in the direction of the arrows on line 6—6 of FIG. 5.
Figure 7:
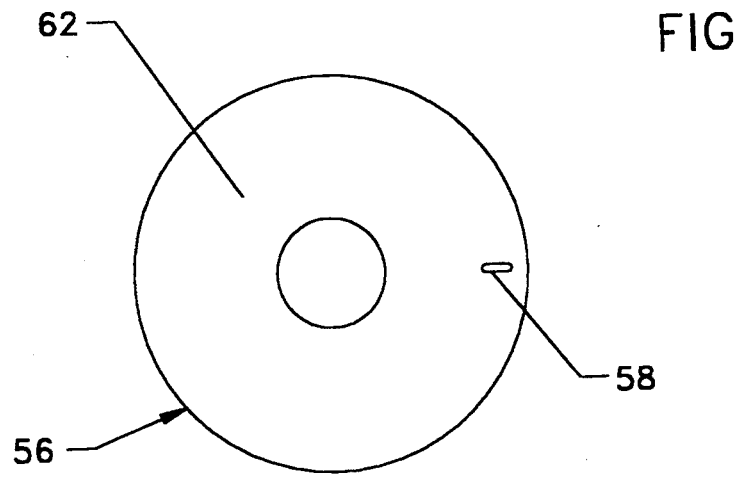
FIG. 7 is a plan view of the face of the distributor rotor for coupling the intake line to selected ports and respective collectors and containers.
Figure 8:
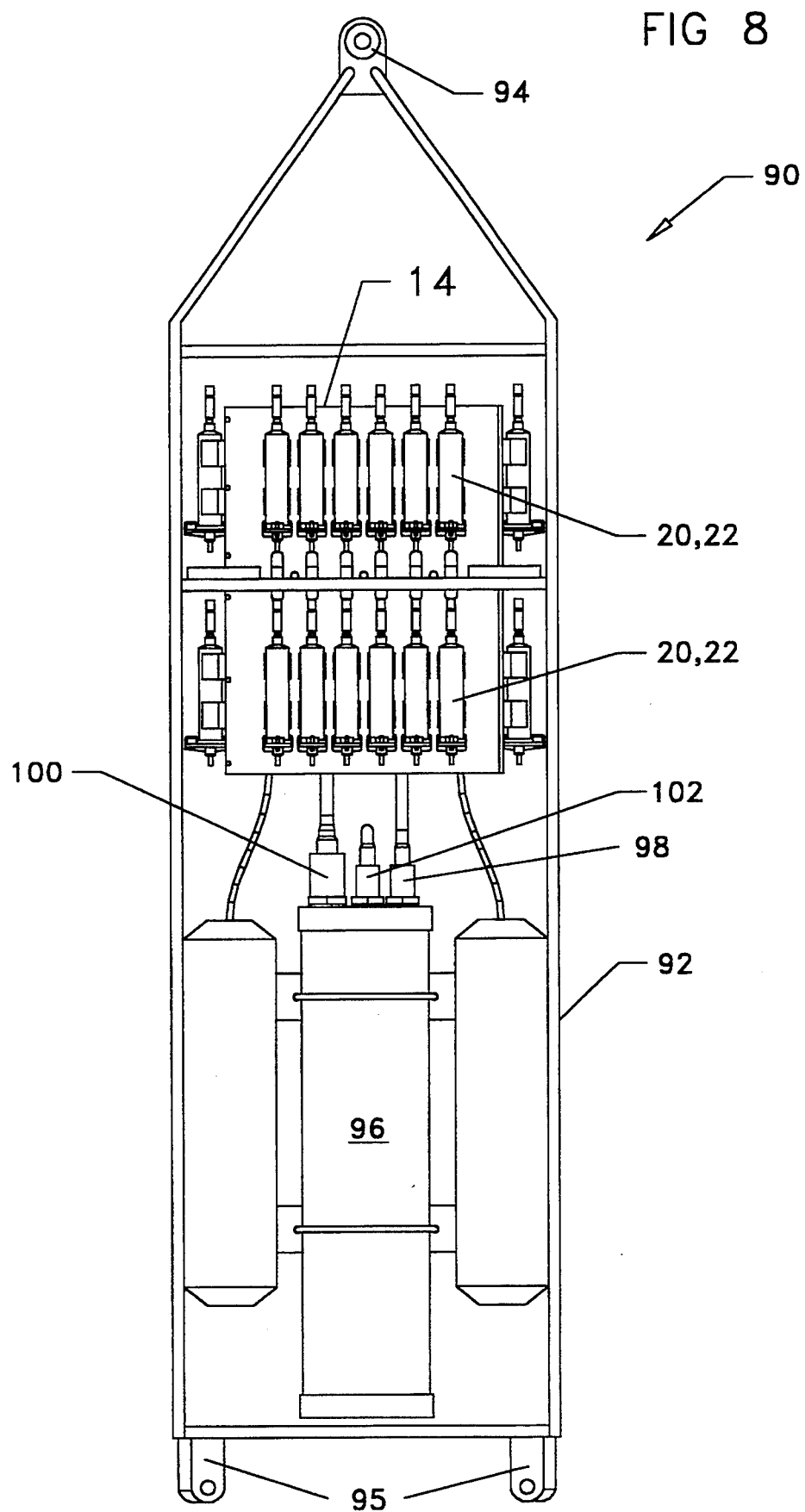
FIG. 8 is a side view and FIG. 9 a plan view of the assembled water collecting instrument.
Figure 9:
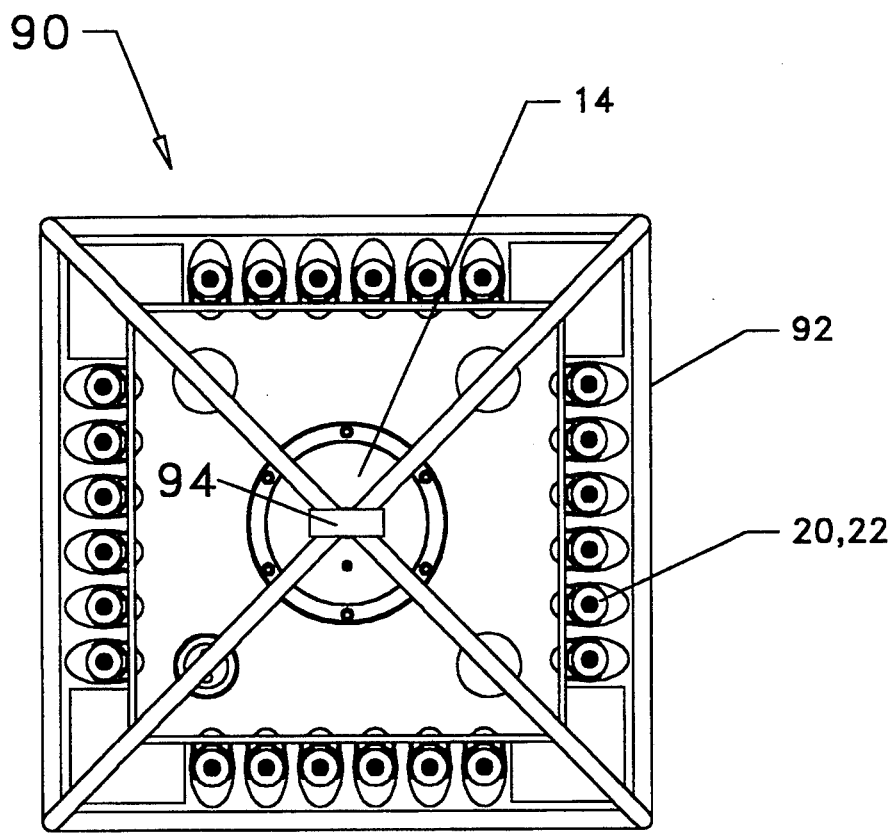

To understand operation of the multiport valve head 50 and distributor rotor 56 of the multiport valve assembly 14 shown in FIG. 5, reference is made to FIGS. 6 and 7, FIG. 6 is a partial cross section through the top of the multiport valve 14 in the direction of the arrows on line 6—6 of FIG. 5, FIG. 6 therefore illustrates the respective bearing surface 60 of the multiport valve head 50, As shown in FIG. 6 the single intake line 15 is coupled to an elongate inlet channel 70 in the configuration of a circular groove 70 concentric with the driven rotating shaft 54. The fifty ports 16 terminate in a ring of fifty holes forming an outer ring 72 concentric with and outside the inner circular groove 70.

FIG. 7 illustrates the bearing surface 62 of the distributor rotor 56. As noted above the rotor 56 rotates with the rotating shaft 54 while the valve head 50 and valve body 52 remain stationary relative to the rotating shaft 54 and rotor 56. The bearing face 62 of rotor 56 is formed with a radial coupling channel 58 in the configuration of a short length of a radial groove having dimensions and radial position for extending a coupling channel between the inner ring circular groove 70 and the outer ring of port holes 16 on the bearing face 60 of the valve head 50. Thus, the radial groove coupling channel 58 is positioned for making selected couplings in a time series sequence between the continuous elongate circular channel 70 coupled to the single intake line 15 and selected port inlets 18 and ports 16 of the outer circle 72. This is accomplished in a controlled sequence determined by instructions from the programmable controller hereafter described.

With respect to construction features of the multiport valve 14 of FIGS. 5–7, the multiport valve head 50 and valve body 52 can be constructed for example from relatively hard Delrin TM plastic. On the other hand the rotor 56 is constructed for example of a softer Teflon TM plastic. The relatively softer and relatively harder flat bearing surfaces 60,62 provide a good seal between the bearing surfaces, sealing off the unused ports 16 of the multiport valve head. Instead of plastic, other materials may be used for the valve head 50 and rotor distributor 56 such as ceramic and graphite materials. More important than the particular materials and relative hardnesses, however, the bearing surfaces are formed with flat faces to achieve the desired sealing engagement.

In order to maintain appropriate pressure between the bearing faces 60,62, the distributor rotor 56 is mounted on shaft 54 with a compression Inconel X750 TM alloy spring 75. The alloy spring 75 is mounted around the rotating shaft 54 bearing against the rotor 56 and a bearing plate 76 of the valve body 52. The spring 75 is selected for example to have a 100 pound spring force assuring a sealing coupling between the bearing surfaces. Various seals throughout the multiport valve are provided by the use of O ring seals 78 at various locations.

With respect to further details of construction, the stepper motor 55 is housed within an oil filled cavity defined by stepper motor housing 80 also constructed from Delrin TM plastic material. The oil filled cavity is also partly defined by an oil bladder or oil diaphragm 82 which is sealed to the external water or other fluid. The diaphragm 82 and oil filled cavity provide pressure compensation for the housing 80 for pressure fluctuations due to ocean depths, for example, up to 5,000 meters. The rotary drive shaft 54 from stepper motor 55 is constructed for example from titanium metal.

By way of example the automated water sampling system of FIGS. 1–4 with multiport valve of FIGS. 5–7 is incorporated in a WSS 90 for time series sequential sampling of sea water at ocean depths up to 5,000 meters. The water sampling system 90 is assembled on a mooring frame 92 with upper and lower mooring eyes 94 and 95. The programmable controller 96 is contained for example in a titanium pressure housing and includes a stepper motor connector 98 for controlling the stepper motor and multiport valve 14, a pump motor connector 100 for controlling the pump 12, not visible, and a communication connector 102 where a personal computer can be coupled for programming the programmable controller 96 and for downloading data from a sample collection time series sequence.

The bank 20 of sample water receivers or containers 22 is shown mounted around the multiport valve 14 with the sample water collectors arranged in an outer double circle for convenient coupling between the respective sample water opening ends of the sample water receivers 22 and the ports 16 of the multiport valve 14. The cleaning liquid container and flushing liquid container are of course also incorporated in the circular configuration of sample water containers.

Prior to deployment of the WSS a schedule of water sampling events is programmed into the programmable controller 96 using, for example, a personal computer. The water sampling events schedule can be entered in several ways. First, the programmable controller 96 can be programmed to specify the time of occurrence of each of the forty-eight or other selected number of water sampling events. Second a start time can be programmed into the controller along with a specified time intervals between sampling events. Third a start time and stop time can be programmed into the controller 96 which will then automatically space the water sampling events between the programmed start and end times.

The water sample containers are loaded on respective holders around the multiport valve with the pistons in position against the water sample opening ends of the respective water sample containers. The water sample containers are backfilled with pumping water to hold the respective pistons in place until a sampling event occurs. On the other hand the cleaning liquid container is loaded with acid cleaning liquid so that the piston rests against the pumping water end of the cleaning liquid container. Similarly the flushing liquid container is filled with distilled water so that the piston also rests against the pumping water opening end of the flushing liquid container. When the WSS 90 is fully prepared it can be deployed and moored in a remote submarine or subaqueous environment in which it is adapted to operate, providing a time series sequence of water samples.

Operation of the WSS 90 is as follows. When the scheduled time for a water sampling event arrives, the programmable controller directs movement of the multiport valve to the acid cleaning liquid port, that is the port 16 coupled to the cleaning liquid container. The pump 12 is actuated to operate in reverse and acid cleaning liquid is forced and injected out the intake line 15. The multiport valve 14 then moves to the distilled water port, that is the port 16 coupled to the flushing liquid container. The pump 12 continues to operate in reverse and distilled water is pushed out of the intake line 15 flushing the intake line of acid cleaning liquid.

The programmable controller then waits for about five minutes so that the acid cleaning liquid and distilled water diffuse into the sea water.

The programmable controller then rotates the multiport valve and couples the intake line to the next available empty water sample receiver or container. The pump 12 is actuated to operate in the forward direction and a water sample fills the water sample container. The multiport valve under direction of the programmable controller then rotates to a position between two of the ports 16 so that all of the ports are sealed from the sea water. In this manner the WSS instrument 90 can be deployed continuously in submarine and subaqueous environments for extended periods for example up to fourteen months.

After retrieving the WSS instrument 90 from a deployed location, water samples are removed from the respective water sample containers by injecting or pumping water against the back side of the piston. Data relevant to the water sampling events is also retrieved from the programmable controller 96 using an external computer and standard communication port such as an RS-232 port. A communications port such as the RS-232 port is also used during programming of the programmable controller 96.

For a use of plastic bags as sample water receivers or containers, the bag is formed with a single opening which is fitted over a respective port 16 or water sampling inlet coupled to the port. Typically a metalized polyethylene bag such as a space shuttle bag is used for the water sample collecting bag. The bag is typically placed in a tube or cylinder accommodating the bag volume of for example 1 liter. When the bag is empty prior to use and deployment in collecting a water sample, the tube or cylinder is filled with water so that the bag is in a collapsed condition. When a scheduled water sampling event occurs, the pump 12 pumps the pumping water out of the tube which causes the sample collecting bag to expand and fill with the water sample.

The WSS 10, 90 of the present invention may be used for a variety of automated water sampling sites for example at remote locations. Water samples may be collected for a variety of research, environmental laboratory, and water analysis purposes and studies such a nutrient levels, $CO_2$ concentrations, dissolved organic matter, trace elements, pollutants, etc. The WSS is applicable for collecting water samples in a variety of marine and limnological environments, oceans, lakes, rivers etc.

While the invention has been described with reference to particular example embodiments it is intended to cover all modifications and equivalents within the scope of the following claims.

We claim:

1. An automated water sampling system for collecting multiple samples of sample water at a remote site comprising:

a multiport valve having a plurality of ports and respective port inlets, a sample water intake line coupled to the respective port inlets, and valve means for individually opening and closing the port inlets;

a plurality of sample receivers coupled to respective ports of the multiport valve;

at least one container of cleaning liquid coupled to a port of the multiport valve;

an output manifold having a plurality of manifold outlets coupled to the respective sample receivers and to said at least one container of cleaning liquid, and a water output line coupled to the plurality of manifold outlets;

a reversible pump coupled to the water output line for pumping and drawing sample water through the intake line into selected sample receivers and for pumping and pushing cleaning liquid from said at least one cleaning liquid container out the sample water intake line;

and a programmable controller coupled to the valve means and pump, said controller being programmable to cause pumping and drawing of sample water into the intake line and into respective sample receivers in series in a timed sequence of sample collecting events, said controller also being programmable for reversing the pump and pumping and pushing cleaning liquid from at least one cleaning liquid container out the intake line to wash away biofouling material between the sample collecting events.

2. The water sampling system of claim 1 wherein the water sample receivers each comprise an elongate container having a sample water opening at one end, a pumping water opening at the other end, and containing a slidable sealing piston slidable between the ends of the elongate container in response to differential pressure across the piston, each elongate container being coupled to a respective port of the multiport valve at the sample water opening end and to a respective manifold outlet of the output manifold at the pumping water opening end.

3. The water sampling system of claim 2 wherein said at least one cleaning liquid container comprises an elongate container having a cleaning liquid opening at one end, a pumping water opening at the other end, and containing a slidable sealing piston slidable between the ends of the elongate container in response to differential pressure across the piston, said elongate container being coupled to a respective port of the multiport valve at the cleaning liquid opening end and to a respective manifold outlet of the output manifold at the pumping water opening end.

4. The water sampling system of claim 3 wherein the initial position of the piston in respective sample receivers before a respective sample collecting event is adjacent to the sample water opening end of the elongate container, and the elongate container is back filled from the pumping water opening end with pumping water, and wherein the starting position of the piston in said at least one cleaning fluid container is adjacent to the pumping water opening end with the elongate container filled with cleaning liquid.

5. The water sampling system of claim 2 wherein the sample receivers are syringes.

6. The water sampling system of claim 2 wherein the sample receivers are sample collecting elongate cylindrical tubes.

7. The water sampling system of claim 2 wherein the sample receivers comprise a flexible bag inside the elongate container, said flexible bag having an opening coupled to the respective port through the sample water opening end of the elongate container.

8. The water sampling system of claim 1 wherein the valve means comprises a valve head having multiple ports and port inlets arranged in substantially circular configuration, and a distributor rotor bearing against the valve head for rotation to different rotational positions, said rotor forming a seal between the rotor and valve head, said distributor rotor being formed with a coupling channel for coupling the sample water intake line to different port inlets and respective ports according to the rotational position of the rotor.

9. The water sampling system of claim 8 wherein the valve ahead and distributor rotor are formed with flat bearing faces for sealing and closing all port inlets and ports when the rotor is in rotational positions with the coupling channel between ports;

wherein the bearing face of the valve head is formed with a circular channel having a first diameter coupled to the water sample intake line;

wherein the bearing face of the valve head is also formed with a circle of holes being the port inlets, said port inlet holes being arranged in a circular ring having a second diameter different from the first diameter of the circular channel but concentric with the circular channel;

and wherein the bearing face of the rotor is formed with a radial coupling channel extending between the circular channel and circular ring of port inlet holes.

10. The water sampling system of claim 3 comprising:

a cleaning liquid container comprising an elongate container of cleaning liquid coupled to a cleaning port of the multiport valve for washing away befouling material from the sample water intake line;

an elongate container of flushing liquid coupled to a flushing port of the multiport valve for flushing away cleaning liquid;

and wherein the controller is also programmable for operating the pump in reverse for first pumping and pushing cleaning liquid out the sample water intake line and then pumping and pushing flushing liquid out the sample water intake line for flushing away cleaning liquid.

11. An automated water sampling system for collecting multiple samples of sample water at a remote site comprising:

a multiport valve having a plurality of ports and respective port inlets, a sample water intake line coupled to the respective port inlets, and valve means for individually opening and closing the port inlets;

a plurality of sample receivers coupled to respective ports of the multiport valve;

the water sample receivers each comprising an elongate container having a sample water opening at one end, a pumping water opening at the other end, and containing a slidable sealing piston slidable between the ends of the elongate container in response to differential pressure across the piston, each elongate container being coupled to a respective port of the multiport valve at the sample water opening end and to a respective manifold outlet of the output manifold at the pumping water opening end;

the initial position of the piston in respective sample receivers before a respective sample collecting event being adjacent to the sample water opening end of the elongate container, and the elongate container being back filled from the pumping water opening end with pumping water;

at least one container of cleaning liquid coupled to a port of the multiport valve, said cleaning liquid container comprising an elongate container having a cleaning liquid opening at one end, a pumping water opening at the other end, and containing a slidable sealing piston slidable between the ends of the elongate container in response to differential pressure across the piston, said elongate container being coupled to a respective port of the multiport valve at the cleaning liquid opening end and to a respective manifold outlet of the output manifold at the pumping water opening end;

and wherein the starting position of the piston in said cleaning fluid container is adjacent to the pumping water opening end with the elongate container filled with cleaning liquid;

an output manifold having a plurality of manifold outlets coupled to the respective sample receivers and to said at least one container of cleaning liquid at the respective pumping water opening ends, and a water output line coupled to the plurality of manifold outlets;

a reversible pump coupled to the water output line for pumping and drawing sample water through the sample water intake line into selected sample receivers and for pumping and pushing cleaning liquid from at least one cleaning liquid container out the sample water intake line;

and a programmable controller coupled to the valve means and pump, said controller being programmable to cause pumping and drawing of sample water into the intake line and into respective sample receivers in series in a timed sequence of sample collecting events, said controller also being programmable for reversing the pump and pumping and pushing cleaning liquid from said at least one cleaning liquid container out the sample water intake line to wash away befouling material between the sample collecting events.

12. The water sampling system of claim 11 wherein the sample receivers are syringes.

13. The water sampling system of claim 11 wherein the sample receivers are sample collecting elongate cylindrical tubes.

14. The water sampling system of claim 11 wherein the sample receivers comprise a flexible bag inside the elongate container, said flexible bag having an opening coupled to the respective port.

15. The water sampling system of claim 11 wherein the valve means comprises a valve head having multiple ports and port inlets arranged in substantially circular configuration and a distributor rotor bearing against the valve head for rotation to different rotational positions, said rotor forming a seal between the rotor and valve head, said distributor rotor being formed with a coupling channel for coupling the sample water intake line to different port inlets according to the rotational position of the rotor; said valve head and distributor rotor being formed with flat bearing faces for sealing and closing all port inlets and ports when the rotor is in rotational positions with the coupling channel between ports.

16. The water sampling system of claim 11 comprising:

a cleaning liquid container comprising an elongate container of cleaning liquid coupled to a cleaning port of the multiport valve for washing away befouling material from the sample water intake line;

an elongate container of flushing liquid coupled to a flushing port of the multiport valve for flushing away cleaning liquid;

and wherein the controller is also programmable for operating the pump in reverse for first pumping and pushing cleaning liquid out the sample water intake line and then pumping and pushing flushing liquid out the sample water intake line for flushing away cleaning liquid.

17. A method for automatically sampling water at a remote site using a multiport valve having a plurality of ports and respective port inlets, a sample water intake line coupled to the respective port inlets, and valve means for individually opening and closing the port inlets comprising:

selectively opening a first port inlet and first port;

pumping and drawing sample water through the sample water intake line and first port inlet into a first sample receiver coupled to the respective first port for collecting a first sample;

closing the first port inlet and first port;

selectively opening a cleaning port inlet and respective cleaning port of the multiport valve;

reversing the pumping direction, pumping and pushing cleaning liquid from a cleaning liquid container coupled to the respective cleaning port out the sample water intake line, and washing away befouling material the cleaning port inlet and respective cleaning port;

waiting a predetermined period of time;

selectively opening a second port inlet and respective second port;

pumping and drawing sample water through the sample water intake line and second port inlet into a second sample receiver coupled to the respective second port for collecting a second sample;

closing the second port inlet and second port;

selectively opening the cleaning port inlet and respective cleaning port;

again reversing the pumping direction, pumping and pushing cleaning liquid from a cleaning liquid container coupled to the respective cleaning port out the sample water intake line, and washing away befouling material;

closing the cleaning port inlet and respective cleaning port;

waiting a predetermined period of time;

and alternating the steps of collecting samples and washing away befouling material in series in a timed sequence until a prescribed number of samples has been collected.

18. The method of claim 17 comprising the steps following the step of closing the cleaning port inlet and respective cleaning port as follows:

selectively opening a flushing port inlet and respective flushing port of the multiport valve;

continuing the reverse pumping direction, pumping and pushing flushing liquid from a flushing liquid container coupled to the respective flushing port out the sample water intake line, and flushing away cleaning liquid from the sample water intake line.

19. The method of claim 17 comprising the steps of providing sample receivers and at least one cleaning liquid container in the configuration of elongate containers having a sample water opening at one end, a pumping water opening at the other end, and containing a slidable sealing piston slidable between the ends of the elongate container in response to differential pressure across the piston;

locating the pistons of sample receivers at the sample water opening end and backfilling the sample receivers with pumping water before the sample collecting steps;

pumping and withdrawing pumping water from a selected sample receiver, sliding the piston from the sample water opening end to the pumping water opening end, and drawing sample water through the sample water intake line into the selected sample receiver for collecting a sample.

20. The method of claim 19 comprising locating the piston of said at least one cleaning liquid container at the pumping water opening end with the container filled with cleaning liquid before the sample collecting steps, pumping and backfilling the cleaning liquid container with pumping water, sliding the piston from the pumping water opening end to the cleaning liquid opening end, pumping and pushing cleaning liquid out the sample water intake line, and washing away befouling material.

21. The method of claim 20 comprising:
providing a flushing liquid container in the same configuration as the cleaning liquid container;
locating the piston of the flushing liquid container at the pumping water opening end with the container filled with distilled water;
pumping and backfilling the flushing liquid container with pumping water, sliding the piston from the pumping water opening end to the flushing liquid opening end, pumping and pushing distilled water out the sample water intake line, and flushing away cleaning liquid.

* * * * *